US010058271B2

(12) United States Patent
Letchner et al.

(10) Patent No.: US 10,058,271 B2
(45) Date of Patent: *Aug. 28, 2018

(54) PHYSICAL ACTIVITY INFERENCE FROM ENVIRONMENTAL METRICS

(71) Applicant: Microsoft Technology Licensing, LLC, Redmond, WA (US)

(72) Inventors: Julia Maureen Letchner, Seattle, WA (US); Scott Saponas, Woodinville, WA (US); Alice Jane Brush, Bellevue, WA (US); Aman Kansal, Redmond, WA (US); Daniel Morris, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/610,247

(22) Filed: May 31, 2017

(65) Prior Publication Data

US 2017/0265783 A1 Sep. 21, 2017

Related U.S. Application Data

(63) Continuation of application No. 13/714,547, filed on Dec. 14, 2012, now Pat. No. 9,700,240.

(51) Int. Cl.
*G08B 23/00* (2006.01)
*A61B 5/11* (2006.01)
(Continued)

(52) U.S. Cl.
CPC ............. *A61B 5/1118* (2013.01); *H04Q 9/00* (2013.01); *A61B 5/18* (2013.01); *A61B 5/6801* (2013.01);
(Continued)

(58) Field of Classification Search
CPC .................. H04W 4/02; H04W 4/023; H04W 4/025–4/028; H04W 4/04; H04L 67/18; H04L 67/22; A61B 5/1118; H04Q 9/00
(Continued)

(56) References Cited

U.S. PATENT DOCUMENTS

| 7,647,195 B1 | 1/2010 | Kahn | |
|---|---|---|---|
| 8,187,182 B2 * | 5/2012 | Kahn | ................... A61B 5/1038 482/1 |

(Continued)

OTHER PUBLICATIONS

Reddy, et al., "Using Mobile Phones to Determine Transportation Modes"—Published Date: Feb. 2010, Proceedings: ACM Transactions on Sensor Networks, vol. 6, No. 2., pp. 1-27, http://www.ee.ucla.edu/~sasank/web/doc/sr_tosn.pdf.
(Continued)

*Primary Examiner* — Thomas Mullen

(57) ABSTRACT

Portable devices include environmental sensors that generate metrics about the environment (e.g., accelerometers detecting impulses and vibration, and GPS receivers detecting position and velocity). Such devices often use environmental metrics to extract user input directed at the device by the user, and status information about the device and the environment. Presented herein are techniques for using environmental metrics to infer physical activities performed by the user while attached to the device. For example, jogging may be inferred from regular, strong impulses and typical jogging speed; walking may be inferred from regular, weak impulses and typical walking speed; and riding in a vehicle may be inferred from low-level vibrations and high speed (optionally identifying the type of vehicle ridden by the user). Based on these inferences, the device may automatically present applications and/or or adjust user interfaces suitable for the user's physical activity, rather than responsive to user input.

20 Claims, 7 Drawing Sheets

(51) Int. Cl.
*H04Q 9/00* (2006.01)
*A61B 5/18* (2006.01)
*A61B 5/00* (2006.01)

(52) U.S. Cl.
CPC ......... *A61B 5/7475* (2013.01); *A61B 2503/12* (2013.01); *A61B 2503/22* (2013.01); *A61B 2560/0247* (2013.01); *A61B 2562/0204* (2013.01); *A61B 2562/0219* (2013.01); *A61B 2562/0223* (2013.01)

(58) Field of Classification Search
USPC ... 340/573.1, 573.4, 539.11–539.13, 539.26, 340/870.16; 702/127, 141; 700/91
See application file for complete search history.

(56) References Cited

U.S. PATENT DOCUMENTS

| | | | | |
|---|---|---|---|---|
| 9,700,240 | B2* | 7/2017 | Letchner | A61B 5/1118 |
| 2009/0132197 | A1* | 5/2009 | Rubin | H04M 1/72563 |
| | | | | 702/141 |
| 2010/0075652 | A1 | 3/2010 | Keskar | |
| 2010/0292921 | A1 | 11/2010 | Zachariah | |
| 2012/0023226 | A1 | 1/2012 | Petersen | |
| 2012/0100895 | A1 | 4/2012 | Priyantha et al. | |
| 2012/0268249 | A1 | 10/2012 | Kansal et al. | |
| 2013/0158686 | A1* | 6/2013 | Zhang | G01C 22/006 |
| | | | | 700/91 |
| 2013/0263127 | A1 | 10/2013 | Arcas et al. | |

OTHER PUBLICATIONS

Kwapisz, et al., "Activity Recognition using Cell Phone Accelerometers"—Published Date: Jul. 25, 2010, Proceedings: 4th International Workshop on Knowledge Discovery from Sensor Data (SensorKDD-201 O), pp. 1-9, http://storm.cis.fordham.edu/~gweiss/papers/sensorKDD-2010.pdf.

Wang, et al., "Accelerometer based transportation mode recognition on mobile phones"—Published Date: Apr. 17, 2010, Proceedings: 2010 Asia-Pacific Conference on Wearable Computing Systems, pp. 44-46, http://ieeexplore.ieee.org/stamp/stamp.jsp?arnumber=05481107.

U.S. Appl. No. 13/714,547, Pre-Interview Office Action dated Aug. 22, 2014, 5 pages.

U.S. Appl. No. 13/714,547, Office Action dated Oct. 10, 2014, 16 pages.

U.S. Appl. No. 13/714,547, Amendment and Response filed Jan. 20, 2015, 34 pages.

U.S. Appl. No. 13/714,547, Office Action dated Mar. 4, 2015, 12 pages.

U.S. Appl. No. 13/714,547, Amendment and Response filed Jul. 6, 2015, 22 pages.

U.S. Appl. No. 13/714,547, Office Action dated Aug. 19, 2015, 9 pages.

U.S. Appl. No. 13/714,547, Amendment and Response filed Feb. 19, 2016, 19 pages.

U.S. Appl. No. 13/714,547, Office Action dated Apr. 6, 2016, 7 pages.

U.S. Appl. No. 13/714,547, Amendment and Response filed Aug. 8, 2016, 11 pages.

U.S. Appl. No. 13/714,547, Office Action dated Oct. 12, 2016, 6 pages.

U.S. Appl. No. 13/714,547, Amendment and Response filed Jan. 19, 2017, 12 pages.

U.S. Appl. No. 13/714,547, Notice of Allowance dated Mar. 1, 2017, 5 pages.

* cited by examiner

PHYSICAL ACTIVITY INFERENCE FROM ENVIRONMENTAL METRICS

CROSS-REFERENCE TO RELATED APPLICATIONS

This application is a continuation application and claims priority to U.S. patent application Ser. No. 13/714,547, filed Dec. 14, 2012 now issued as U.S. Pat. No. 9,700,240, entitled "PHYSICAL ACTIVITY INFERENCE FROM ENVIRONMENTAL METRICS," which application is incorporated herein by reference in its entirety.

BACKGROUND

Within the field of computing, many scenarios involve devices that are used during a variety of physical activities. As a first example, a music player may play music while a user is sitting at a desk, walking on a treadmill, or jogging outdoors. The environment and physical activity of the user may not alter the functionality of the device, but it may be desirable to design the device for adequate performance for a variety of environments and activities (e.g., headphones that are both comfortable for daily use and sufficiently snug to stay in place during exercise). As a second example, a mobile device, such as a phone, may be used by a user who is stationary, walking, or riding in a vehicle. The mobile computer may store a variety of applications that a user may wish to utilize in different contexts (e.g., a jogging application that may track the user's progress during jogging, and a reading application that the user may use while seated). To this end, the mobile device may also feature a set of environmental sensors that detect various properties of the environment that are usable by the applications. For example, the mobile device may include a global positioning system (GPS) receiver configured to detect a geographical position, altitude, and velocity of the user, and a gyroscope or accelerometer configured to detect a physical orientation of the mobile device. This environmental data may be made available to respective applications, which may utilize it to facilitate the operation of the application.

Additionally, the user may manipulate the device as a form of user input. For example, the device may detect various gestures, such as touching a display of the device, shaking the device, or performing a gesture in front of a camera of the device. The device may utilize various environmental sensors to detect some environmental metrics that reveal the actions communicated to the device by the user, and may extract user input from these environmental metrics.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

While respective applications of a mobile device may utilize environmental metrics received from environmental sensors in various ways, it may be appreciated that this environmental information is typically used to indicate the status of the device (e.g., the geolocation and orientation of the device may be utilized to render an "augmented reality" application) and/or the status of the environment (e.g., an ambient light sensor may detect a local light level in order to adjust the brightness of the display). However, this information is not typically utilized to determine the activity of the user. For example, when the user transitions from walking to riding in a vehicle, the user may manually switch from a first application that is suitable for the context of walking (e.g., a pedestrian mapping application) to a second application that is suitable for the context of riding (e.g., a driving directions mapping application). While each application may use environmental information in the selected context, the task of selecting and switching among applications to suit the context of the user may performed through user input. However, it may be appreciated that the physical activities of the user may be determinable automatically according to the environmental metrics.

Presented herein are techniques for configuring a device to infer a physical activity of the user, based on the environmental metrics provided by the environmental sensors. For example, the device may include a classifier utilizing a set of activity profiles that respectively identify the types of environmental metrics that are detectable when a user performs a particular physical activity while the device is attached to the user. At any point in time (e.g., upon receiving a request from an application), the device may receive some environmental metrics from the environmental sensors (exclusive of any environmental metrics comprising user input received from the user), and may invoke the classifier to infer the physical activity performed by the user at that time. This inference may be used to adjust the operation of the device, e.g., by invoking an application and/or adapting the user interface of an application in view of the physical activity of the user.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
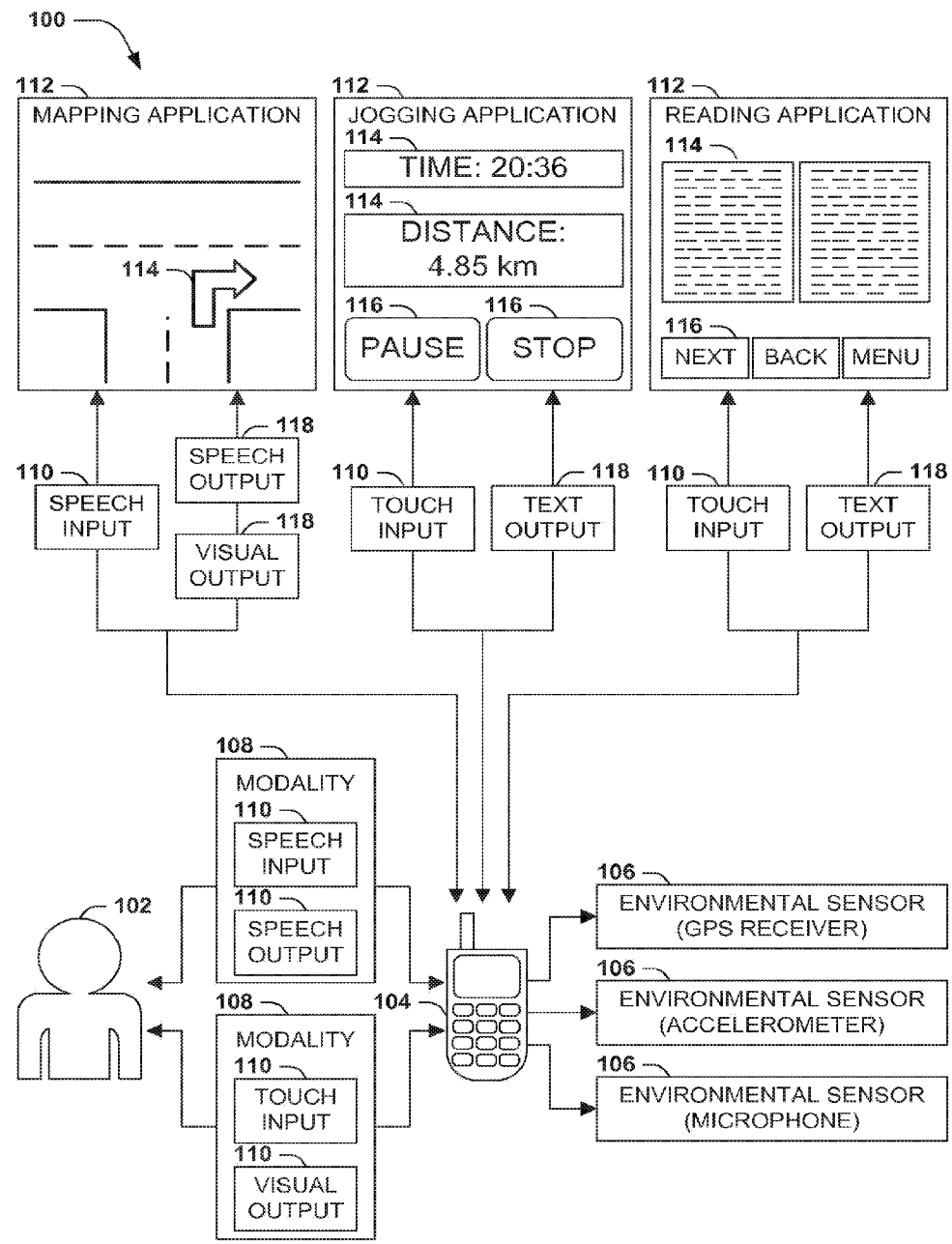
FIG. 1 is an illustration of an exemplary scenario featuring a device comprising a set of environmental sensors and configured to execute a set of applications.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A. Introduction

Within the field of computing, many scenarios involve a mobile device operated by a user in a variety of contexts and environments. As a first example, a music player may be operated by a user during exercise and travel, as well as while stationary. The music player may be designed to support use in variable environments, such as providing solid-state storage that is less susceptible to damage through movement; a transflective display that is visible in both indoor and outdoor environments; and headphones that are both comfortable for daily use and that stay in place during rigorous exercise. While not altering the functionality of the device between environments, these features may promote the use of the mobile device in a variety of contexts. As a second example, a mobile device may offer a variety of applications that the user may utilize in different contexts, such as travel-oriented applications, exercise-oriented applications, and stationary-use applications. Respective applications may be customized for a particular context, e.g., by presenting user interfaces that are well-adapted to the use context.

FIG. 1 presents an illustration of an exemplary scenario 100 featuring a device 104 operated by a user 102 and usable in different contexts. In this exemplary scenario 100, the device 104 features a mapping application 112 that is customized to assist the user 102 while traveling on a road, such as by automobile or bicycle; a jogging application 112, which assists the user 102 in tracking the progress of a jogging exercise, such as the duration of the jog, the distance traveled, and the user's pace; and a reading application 112, which may present documents to a user 102 that are suitable for a stationary reading experience. The device 104 may also feature a set of environmental sensors 106, such as a global positioning system (GPS) receiver configured to identify a position, altitude, and velocity of the device 104; an accelerometer or gyroscope configured to detect a tilt orientation of the device 104; and a microphone configured to receive sound input. Additionally, respective applications 112 may be configured to utilize the information provided by the environmental sensors 106. For example, the mapping application 112 may detect the current location of the device in order to display a localized map; the jogging application 112 may detect the current speed of the device 104 through space in order to track distance traveled; and the reading application 112 may use a light level sensor to detect the light level of the environment, and to set the brightness of a display component for comfortable viewing of the displayed text.

Additionally, respective applications 112 may present different types of user interfaces that are customized based on the context in which the application 112 is to be used. Such customization may include the use of the environmental sensors 106 to communicate with the user 102 through a variety of modalities 108. For example, a speech modality 108 may include speech user input 110 received through the microphone and speech output 118 produced through a speaker, while a visual modality 108 may comprise touch user input 110 received through a touch-sensitive display component and visual output 118 presented on the display. In these ways, the information provided by the environmental sensors 106 may be used to receive user input 110 from the user 102, and to output 118 information to the user 102. In some such devices 104, the environmental sensors 106 may be specialized for user input 110; e.g., the microphone may be configured for particular sensitivity to receive voice input and to distinguish such voice input from background noise.

Moreover, respective applications 112 may be adapted to present user interfaces that interact with the user 102 according to the context in which the application 112 is to be used. As a first example, the mapping application 112 may be adapted for use while traveling, such as driving a car or riding a bicycle, wherein the user's attention may be limited and touch-based user input 110 may be unavailable, but speech-based user input is suitable. The user interface may therefore present a minimal visual interface with a small set of large user interface elements 114, such as a simplified depiction of a road and a directional indicator. More detailed information may be presented as speech output, and the application 112 may communicate with the user 102 through speech-based user input 110 (e.g., voice-activated commands detected by the microphone), rather than touch-based user input 110 that may be dangerous while traveling. The application 112 may even refrain from accepting any touch-based input in order to discourage distractions. As a second example, the jogging application 112 may be adapted for the context of a user 102 with limited visual availability, limited touch input availability, and no speech input availability. Accordingly, the user interface may present a small set of large user interface elements 114 that may be received through a brief glance, and a small set of large user interface controls 116, such as large buttons that may be activated with low-precision touch input. As a third example, the reading application 112 may be adapted for a reading environment based on a visual modality 108 involving high visual input and precise touch-based user input 110, but reducing audial interactions that may be distracting in reading environments such as a classroom or library. Accordingly, the user interface for the reading application 112 may interact only through touch-based user input 110 and textual user interface elements 114, such as highly detailed renderings of text. In this manner, respective applications 112 may utilize the environmental sensors 106 for environment-based context and for user input 110 received from the user 102, and may present user interfaces that are well-adapted to the context in which the application 112 is to be used.

B. Presented Techniques

The exemplary scenario 100 of FIG. 1 presents several advantageous uses of the environmental sensors 106 to facilitate the applications 112, and several adaptations of the user interface elements 114 and user interface controls 116 of respective applications 112 to suit the context in which the application 112 is likely to be used. In particular, as used in the exemplary scenario 100 of FIG. 1, the output of the environmental sensors 106 is are related to the status of the device 104 (e.g., its position or orientation), the status of the environment (e.g., the sound level), or explicit communication with the user 102 (e.g., touch-based or speech-based user input 110). However, the output of the environmental sensors 106 may also be used as a source of information about the status of the user 102 while using the device 104. That is, while the device 104 is attached to the user 102, the movements of the user 102 and environmental changes caused thereby may enable an inference as to the physical activities performed by the user 102. The functionality of the device 104 may therefore be adjusted to satisfy the physical activity of the user 102. For example, the device 104 may automatically (i.e., without prompting from the user 102) present an application 112 relating to the physical activity, or may adjust the user interface elements 114 and/or user interface controls 116 to suit the physical activity of the user 102. Notably, these effects are not achieved as responses to user input 110—e.g., on data from the environmental sensors 106 from which user input 110 directed by the user 102 to the device 104 is extracted (e.g., an explicit user selection of a "Traveling" application or mode)—but, rather, on environmental metrics from which the physical activity of the user is inferred.

Figure 2:
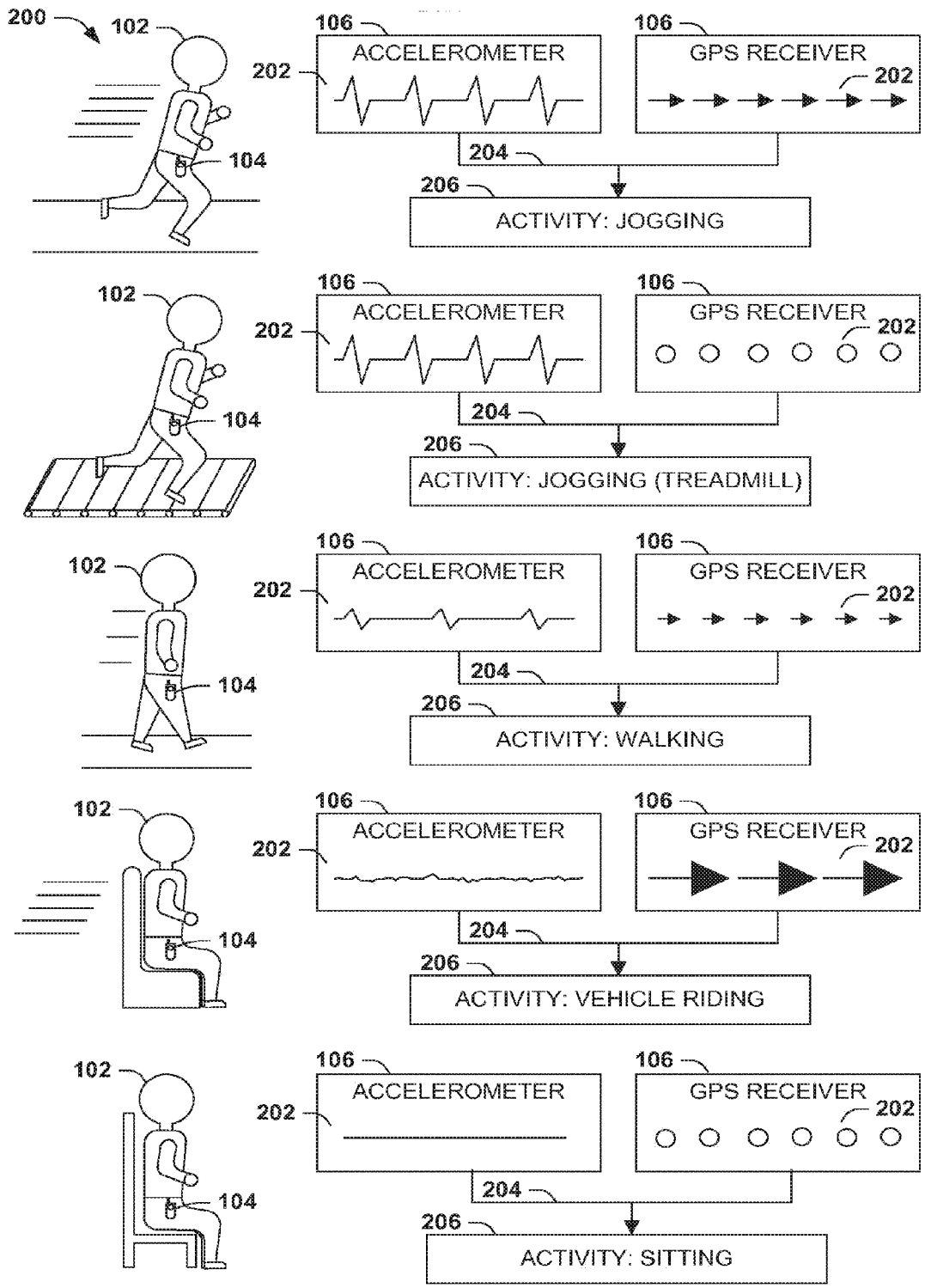
FIG. 2 is an illustration of an exemplary scenario featuring an inference of a physical activity of a user through environmental metrics according to the techniques presented

FIG. 2 presents an illustration of an exemplary scenario 200 featuring a detection of physical activities 206 performed by a user 102 of a device 104 based on environmental metrics 202 reported by respective environmental sensors 106, including an accelerometer and a global positioning system (GPS) receiver. As a first example, the user 102 may perform a jogging physical activity 206 while attached to the device 104. Even when the user 102 is not interacting with the device 104, the environmental sensors 106 may detect various properties of the environment that enable an inference 204 of this physical activity 206. For example, the accelerometer may detect environmental metrics 202 indicating a modest repeating impulse caused by the user's footsteps while jogging, while the GPS receiver also detects a speed that is within the typical speed of jogging physical activities 206. Based on these environmental metrics 202, the device 104 may therefore perform an inference 204 of the jogging physical activity 206 of the user 102. As a second example, the user 102 may perform a jogging exercise on a treadmill. While the accelerometer may detect and report the same pattern of modest repeating impulses, the GPS receiver may indicate that the user 102 is stationary. The device 104 may therefore perform an evaluation resulting in an inference 204 of a treadmill jogging physical activity 206. As a third example, a walking physical activity 206 may be inferred from a first environmental metric 202 of a regular set of impulses having a lower magnitude than for the jogging physical activity 206 and a steady but lower-speed direction of travel indicated by the GPS receiver. As a fourth example, when the user 102 is seated on a moving vehicle such as a bus, the accelerometer may detect a latent vibration (e.g., based on road unevenness) and the GPS receiver may detect high-velocity directional movement, leading to an inference 204 of a vehicle riding physical activity 206. As a fifth example, when the user 102 is seated and stationary, the accelerometer and GPS receiver may both indicate very-low-magnitude environmental metrics 202, and the device 104 may reach an inference 204 of a stationary physical activity 206. Based on these inferences 204 of the physical activity 206 of the user 102 (not involving user input 110 from the user 102 that explicitly specifies the physical activity 202), the device 104 may present applications 112 and user interfaces particularly well-suited for the physical activity 206 in accordance with the techniques presented herein.

C. Exemplary Embodiments

Figure 3:
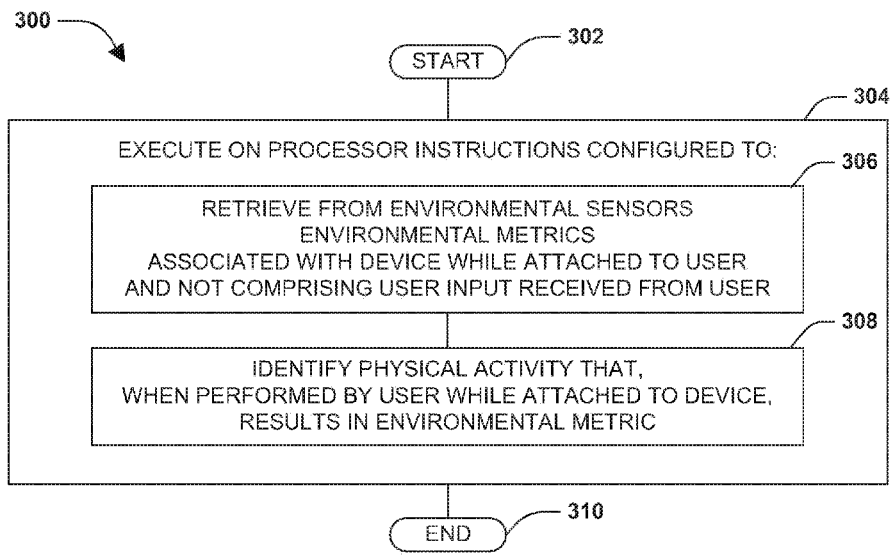
FIG. 3 is a flow chart illustrating an exemplary method of inferring physical activities of a user based on environmental metrics.

FIG. 3 presents a first exemplary embodiment of the techniques presented herein, illustrated as an exemplary method 300 of identifying a physical activity 206 of a user 102 of a device 104. The exemplary method 300 may be implemented, e.g., as a set of processor-executable instructions stored in a memory component of the device 104 (e.g., a memory circuit, a solid-state storage device, a platter of a hard disk drive, or a magnetic or optical device) that, when executed on a processor of the device, cause the device to operate according to the techniques presented herein. The exemplary method 300 begins at 302 and involves executing 304 the instructions on the processor. Specifically, the instructions may be configured to retrieve 306 from at least one environmental sensor 106 at least one environmental metric 202 that is associated with the device 402 while attached to the user 102, and where such environmental metrics 202 do not comprise user input 110 received from the user 102. The instructions may also be configured to identify 308 a physical activity 206 that, when performed by the user 102 while attached to the device 104, results in the at least one environmental metric 202. The device 104 may then utilize the inference 204 of the physical activity 206 to many ends; and by inferring the physical activity 206 based not on user input 110 but on the evaluation of the environmental metrics 202, the exemplary method 300 operates according to the techniques presented herein, and so ends at 310.

Figure 4:
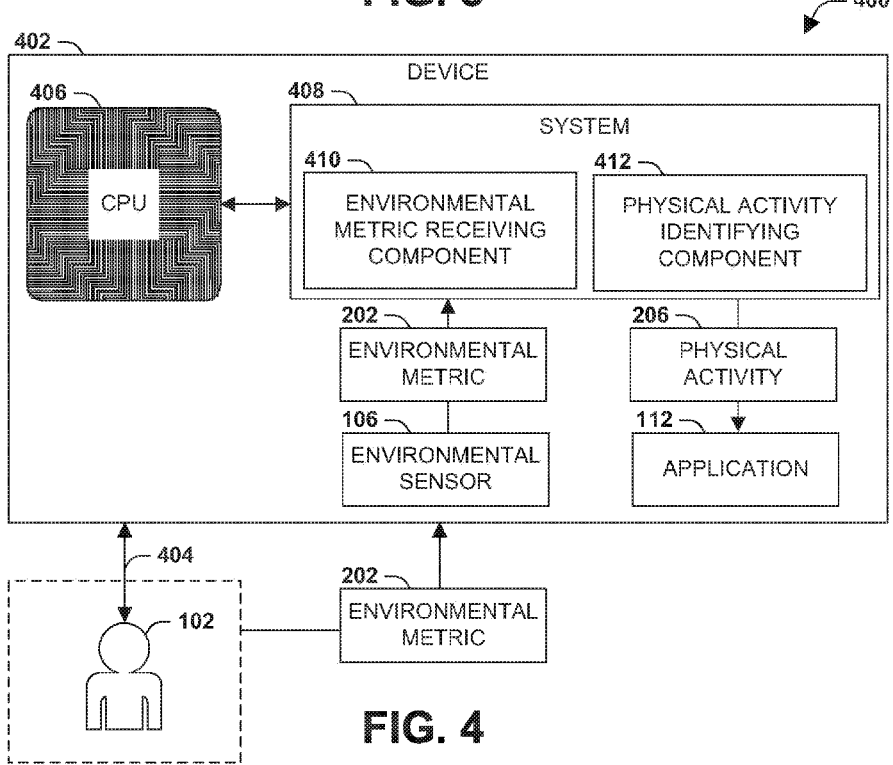
FIG. 4 is a component block diagram illustrating an exemplary system for inferring physical activities of a user based on environmental metrics.

FIG. 4 presents a second embodiment of the techniques presented herein, illustrated as an exemplary scenario 400 featuring an exemplary system 408 configured to identify physical activities 206 performed by a user 102 of a device 402 comprising at least one environmental sensor 106, executing at least one application 112, and having an attachment 404 to the user 102. The exemplary system 408 may be implemented, e.g., as a set of processor-executable instructions stored in a memory component of the device 402 (e.g., a memory circuit, a solid-state storage device, a platter of a hard disk drive, or a magnetic or optical device) that, when executed on a processor 406 of the device 402, cause the device 402 to operate according to the techniques presented herein. The exemplary system 408 comprises an environmental metric receiving component 410 that is configured to, while the user 102 is performing a physical activity 206, receive from respective environmental sensors 106 at least one environmental metric 202 not comprising user input 110 received from the user 102. The exemplary system 408 also includes a physical activity identifying component 412 that is configured to, using the environmental metrics 202, identify the physical activity 206 performed by the user 102, and report the physical activity 206 of the user 102 to the application 112. Having achieved the identification of the physical activity 206 based on an inference from the environmental metrics 202, the exemplary system 408 causes the device 402 to operate according to the techniques presented herein.

Still another embodiment involves a computer-readable medium comprising processor-executable instructions configured to apply the techniques presented herein. Such computer-readable media may include, e.g., computer-readable storage media involving a tangible device, such as a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a CD-R, DVD-R, or floppy disc), encoding a set of computer-readable instructions that, when executed by a processor of a device, cause the device to implement the techniques presented herein. Such computer-readable media may also include (as a class of technologies that are distinct from computer-readable storage media) various types of communications media, such as a signal that may be propagated through various physical phenomena (e.g., an electromagnetic signal, a sound wave signal, or an optical signal) and in various wired scenarios (e.g., via an Ethernet or fiber optic cable) and/or wireless scenarios (e.g., a wireless local area network (WLAN) such as WiFi, a personal area network (PAN) such as Bluetooth, or a cellular or radio network), and which encodes a set of computer-readable instructions that, when executed by a processor of a device, cause the device to implement the techniques presented herein.

Figure 5:
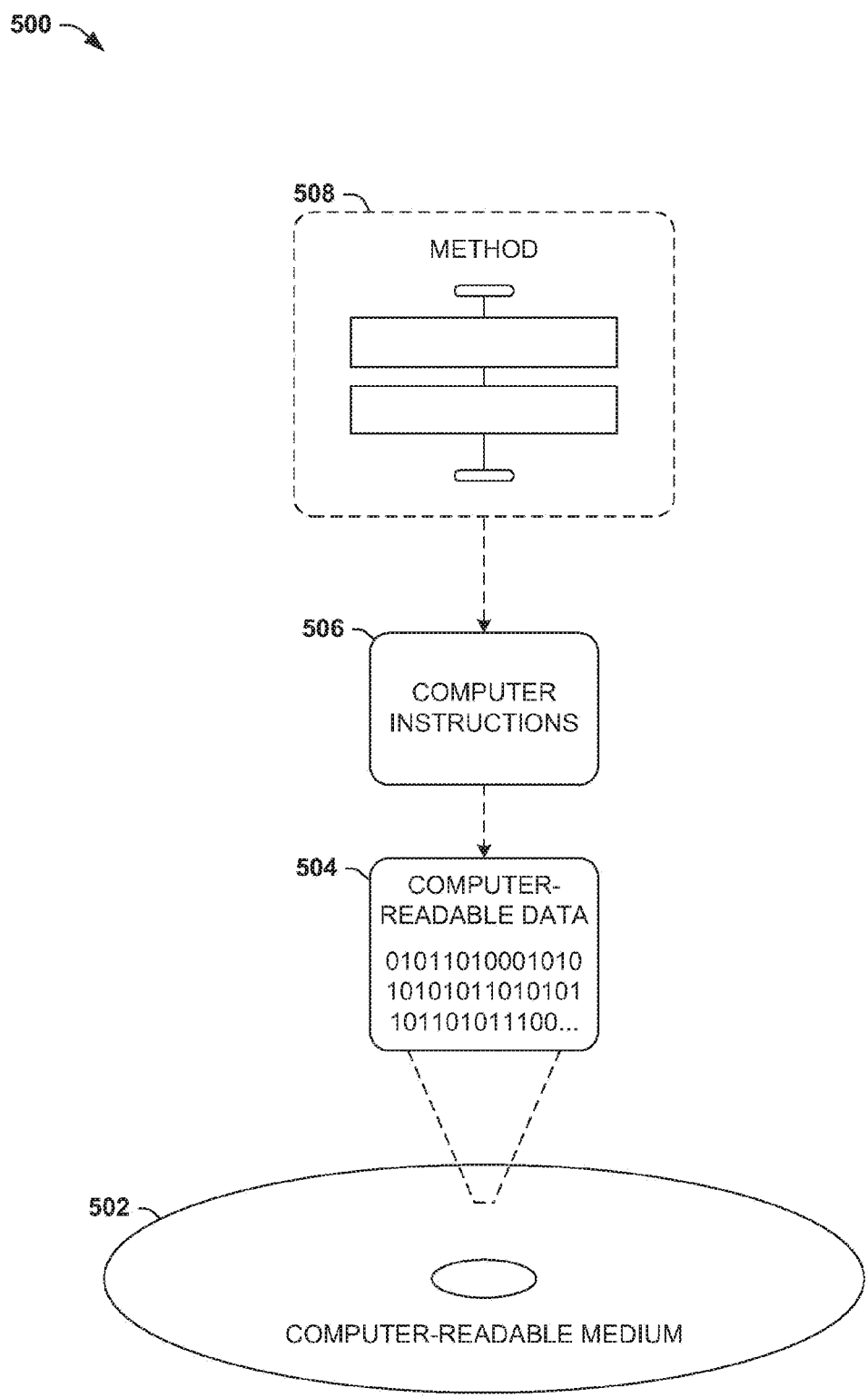
FIG. 5 is an illustration of an exemplary computer-readable medium comprising processor-executable instructions configured to embody one or more of the provisions set forth herein.

An exemplary computer-readable medium that may be devised in these ways is illustrated in FIG. 5, wherein the implementation 500 comprises a computer-readable medium 502 (e.g., a CD-R, DVD-R, or a platter of a hard disk drive), on which is encoded computer-readable data 504. This computer-readable data 504 in turn comprises a set of computer instructions 506 configured to operate according to the principles set forth herein. In one such embodiment, the processor-executable instructions 506 may be configured to perform a method 508 of inferring physical activities of a user based on environmental metrics, such as the exemplary method 300 of FIG. 3. In another such embodiment, the processor-executable instructions 506 may be configured to implement a system for inferring physical activities of a user based on environmental metrics, such as the exemplary system 408 of FIG. 4. Some embodiments of this computer-readable medium may comprise a nontransitory computer-readable storage medium (e.g., a hard disk drive, an optical disc, or a flash memory device) that is configured to store processor-executable instructions configured in this manner. Many such computer-readable media may be devised by those of ordinary skill in the art that are configured to operate in accordance with the techniques presented herein.

D. Variations

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in various embodiments (e.g., the exemplary method 300 of FIG. 3 and the exemplary system 408 of FIG. 4) to confer individual and/or synergistic advantages upon such embodiments.

D1. Scenarios

A first aspect that may vary among embodiments of these techniques relates to the scenarios wherein such techniques may be applied.

As a first variation of this first aspect, the techniques presented herein may be used with many types of devices 104, including mobile phones, tablets, personal information manager (PIM) devices, portable media players, portable game consoles, and palmtop or wrist-top devices. Additionally, these techniques may be implemented by a first device that is in communication with a second device that is attached to the user 102 and comprises the environmental sensors 106. The first device may comprise, e.g., a physical activity identifying server, which may evaluate the environmental metrics 202 provided by the first device, arrive at an inference 204 of a physical activity 206, and inform the first device of the inferred physical activity 206. The device 104 may also have many types of attachment 404 to the user 102, such as being carried by the user 102, stowed in a pocket or bag, worn, attached to clothing, integrated with clothing (such as shoes, vision-correcting glasses, sunglasses, and goggles), and/or embedded in the human body.

As a second variation of this first aspect, the techniques presented herein may be used with many types of environmental sensors 106 providing many types of environmental metrics 202 about the environment of the user 102. For example, the environmental metrics 202 may be generated by one or more environmental sensors 106 selected from an environmental sensor set comprising a global positioning system (GPS) receiver configured to generate a geolocation metric, a linear velocity metric, and/or an acceleration metric; a gyroscope configured to generate an angular velocity metric; a touch sensor configured to detect touch input that does not comprise user input (e.g., an accidental touching of a touch-sensitive display, such as the palm of a user who is holding the device); a wireless communication signal sensor configured to generate a wireless communication signal metric (e.g., a cellular signal strength metric, which may be indicative of the distance of the device 104 from a wireless communication signal source at a known location); a gyroscope or accelerometer configured to generate a device orientation metric (e.g., a tilt impulse, or vibration metric); an optical sensor, such as a camera, configured to generate a light level metric; a microphone configured to generate a sound level metric; a magnetometer configured to detect a magnetic field metric; and an impedance sensor configured to detect moisture contacting the device 104. Moreover, a combination of such environmental sensors 106 may enable a set of overlapping and/or discrete environmental metrics 202 that provide a more robust indication of the physical activity 206 of the user 102.

As a third variation of this first aspect, the techniques presented herein may enable the inference 204 of many types of physical activities 206 of the user 102. As a first example, a walking physical activity 206 may be inferred from a regular set of impulses of a medium magnitude and/or a speed of approximately four kilometers per hour. As a second example, a jogging physical activity 206 may be inferred from a faster and higher-magnitude set of impulses and/or a speed of approximately six kilometers per hour. As a third example, a standing physical activity 206 may be inferred from a zero velocity, neutral impulse readings from an accelerometer, a vertical tilt orientation of the device 104, and optionally a dark reading from a light sensor indicating the presence of the device in a hip pocket, while a sitting physical activity 206 may provide similar environmental metrics 202 but may be distinguished by a horizontal tilt orientation of the device 104. As a fourth example, a swimming physical activity may be inferred from an impedance metric indicating the immersion of the device 104 in water. As a fifth example, a bicycling physical activity 206 may be inferred from a regular circular tilt motion indicating a stroke of an appendage to which the device 104 is attached and a speed exceeding typical jogging speeds. As a sixth example, a vehicle riding physical activity 206 may be inferred from a background vibration (e.g., created by uneven road surfaces) and a high speed. Moreover, in some such examples, the device 104 may further infer, along with a vehicle riding physical activity, at least one vehicle type that, when the vehicle riding physical activity is performed by the user 102 while attached to the device and while the user 102 is riding in a vehicle of the vehicle type, results in the environmental metric 202. For example, the velocity, rate of acceleration, and magnitude of vibration may distinguish when the user 102 is riding on a bus, in a car, or on a motorcycle. These and other types of physical activities 206 may be inferred in accordance with the techniques presented herein.

D2. Activity Inference

A second aspect that may vary among embodiments of these techniques relates to the manner of reaching an inference 204 of a physical activity 206 from one or more environmental metrics 202.

As a first variation of this second aspect, the activity inference may be achieved using many types of classifier logic. As a first example of this first variation, the inference 204 may utilize one or more physical activity profiles that are configured to correlate environmental metrics 202 with physical activities 206, and that may be invoked to select a physical activity profile matching the environmental metrics 202 in order to infer a physical activity 206. As a first example of this first variation, the classifier logic may comprise a set of one or more physical activity profiles that respectively indicate a value or range of an environmental metric 202 that may enable an inference 204 of a physical activity 206 (e.g., a specified range of accelerometer impulses and speed indicating a jogging physical activity 206). The physical activity profiles may be generated by a user 102, automatically generated by one or more statistical correlation techniques, and/or a combination thereof, such as manual tuning by a user of automatically generated physical activity profiles. The device 104 may then infer a physical activity 206 by comparing a set of collected environmental metrics 202 with those of the physical activity profiles in order to identify a selected physical activity profile. As a second example of this first variation, the classifier logic may comprise an ad hoc classification technique, e.g., an artificial neural network or a Bayesian statistical classifier. For example, the device 104 may comprise a training data set that identifies sets of environmental metrics 202 as well as the physical activity 206 resulting in such environmental metrics 202. The classifier logic may be trained using the training data set until it is capable of recognizing such physical activities 206 with an acceptable accuracy.

As a second variation of this second aspect, the accuracy of the inference 204 of the physical activity 206 may be sharpened through many techniques. As a first example of this second variation, respective physical activities 206 may be associated with respective environmental metrics 202 according to an environmental metric significance, indicating the significance of the environmental metric to the inference 204 of the physical activity 206. For example, a device 104 may comprise an accelerometer and a GPS receiver. A vehicle riding physical activity 206 may place higher significance on the speed detected by the GPS receiver than the accelerometer (e.g., if the user device 104 is moving faster than speeds achievable by an unassisted human, the vehicle riding physical activity 206 may be automatically selected). On the other hand, a specific set of highly distinctive impulses may be indicative of a jogging physical activity 206 at a variety of speeds, and thus may place higher significance on the environmental metrics 202 generated by the accelerometer than those generated by the GPS receiver. The inference 204 performed by the classifier logic may accordingly weigh the environmental metrics 202 according to the environmental metric significances for respective physical activities 206.

As a second example of this second variation, the classifier logic may be further configured to, in addition to selecting a physical activity 206, identify a selection confidence of the selection of the physical activity 206 associated with the environmental metrics 202. For example, the device 104 may define an acceptable confidence level threshold in selecting one physical activity 206 over other physical activities 206 (e.g., 90% confidence in an accurate inference 204), and may only report the inferred physical activity 206 if the selection confidence exceeds the acceptable confidence level threshold. Additionally, if the selection confidence is low, the device 104 may collect at least one additional environmental metric 202 from the environmental sensors 106 (e.g., continuing to sample the environment of the user 102 and the device 104), and may apply the classifier logic to the combination of the set of additional environmental metrics 202 and the initial set of environmental metrics 202 in order to achieve an acceptably accurate inference 204.

As a third example of this second variation, the device 104 may interact with the user 102 to determine the physical activity 206 represented by a set of environmental metrics 202. For example, if the environmental metrics 202 are difficult to correlate with any currently identified physical activity 206, or if the user 102 performs a currently identified physical activity 206 in a peculiar or user-specific manner that leads to difficult-to-infer environmental metrics 202, the device 104 may ask the user 102, or a third user (e.g., as part of a "mechanical Turk" solution), to identify the physical activity 206 resulting in the reported environmental metrics 202. Upon receiving a user identification of the physical activity 206, the device 104 may adjust the classifier logic in order to achieve a more accurate identification of the physical activity 206 of the user 102 upon next encountering similar environmental metrics 202.

As a third variation of this second aspect, the inference 204 may be performed using many architectures. As a first such example, the device 104 performing the inference 204 may be attached to the environmental sensors 106, or may be in wireless communication with environmental sensors 106 attached to the user 102. As a second such example, the inference 204 may be performed by a first device that is in communication with a second device associated with the environmental sensors 106, such as a computer of the user 102 or a physical activity identifying service provided over a network such as the internet. For example, a device 104 may send the environmental metrics 202 to the service, which may evaluate the environmental metrics 202, perform an inference of a physical activity 206, and send the physical activity 206 back to the device. Alternatively, the physical activity identifying service may provide a classifier logic to the device, which may apply the classifier logic to perform the inference 204. In either scenario, the second device or physical activity identifying service may adjust the classifier logic (e.g., upon receiving environmental metrics 202 associated with a new physical activity 206, the device 104 and/or physical activity identifying service may adjust the inference 204 in order to infer the physical activity 206 accurately for these environmental metrics 202 in the future).

Figure 6:
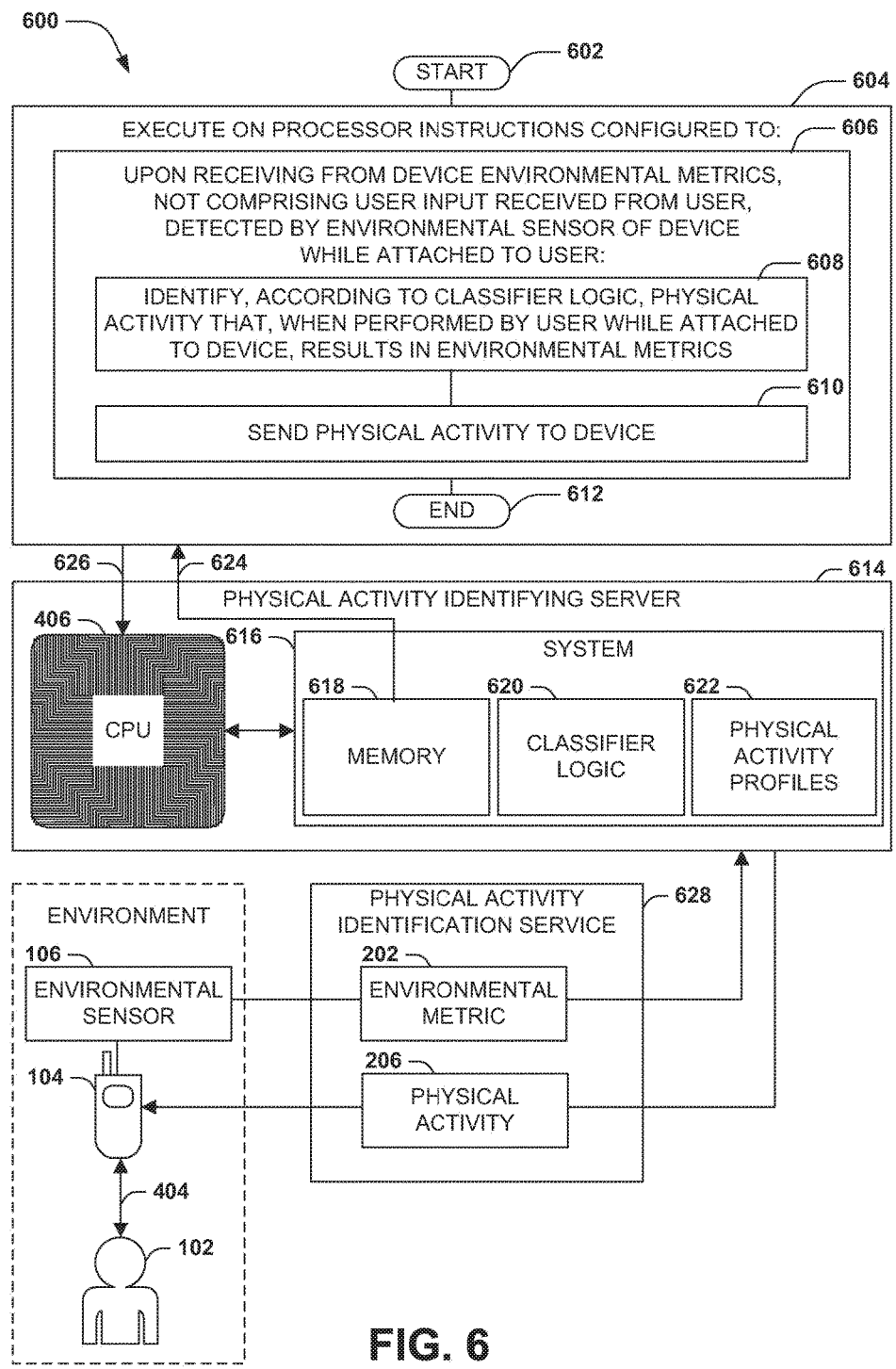
FIG. 6 is an illustration of an exemplary scenario featuring a physical activity identifying service configured to assist a device in the identification of physical activities of a user based on environmental metrics.

FIG. 6 presents an illustration of an exemplary scenario 600 featuring several of the variations of the techniques described herein. In this exemplary scenario 600, a physical activity identifying server 614 is provided and configured to provide a physical activity identification service 628 that identifies physical activities 206 from environmental metrics 202 reported by various devices 104. For example, while a user 102 performs a physical activity 206, a device 104 having an attachment 404 to the user 102 may apply an environmental sensor 106 to generate one or more environmental metrics 202, which the device 104 may send to the physical activity identifying server 614 (e.g., via a wireless communication link to the internet). The physical activity identifying server 614 may comprise a processor 406 and a system 616 including a memory 618, a classifier logic 620, and a set of physical activity profiles 622. The memory 618 may also comprise instructions executable by the processor 406, and upon receiving the environmental metrics 202, may perform 624 the exemplary method beginning at 602 by executing 604 the instructions 626 on the processor 406. In particular, the instructions stored in the memory 618 may cause the physical activity identifying server 614 to, upon receiving 606 from the device environmental metrics not comprising user input received from the user, wherein the environmental metrics are detected by the environmental sensor of the device while attached to the user, identify 608, according to the classifier logic 620, a physical activity 206 that, when performed by the user 102 while having an attachment 404 to the device 104, results in the environmental metric 202. The classifier logic 620 may achieve this identification, e.g., by comparing the environmental metrics 202 with those specified in respective physical activity profiles 622, and, optionally, may adjust its physical activity profiles 622 in view of the inference for this environmental metric 202. The physical activity identifying server 614 may then send 610 the physical activity 206 to the device 104, which may adjust its operation to suit the physical activity 206 of the user 102. In this manner, the device 104 and the physical activity identifying server 614 may interoperate to achieve the inference of the physical activity 206 from the environmental metric 202. Many variations of this exemplary scenario 600 and other such scenarios may be devised by those of ordinary skill in the art while implementing the techniques presented herein.

D3. Uses of Physical Activity Inference

A third aspect that may vary among embodiments of these techniques relates to the configuration of the device 104 to respond to the inferred physical activity 206 of the user 102.

As a first variation of this third aspect, the device 104 may, upon identifying a newly initiated physical activity 206, identify an application 112 associated with the physical activity 206, and invoke the application 112. For example, upon identifying a jogging physical activity 206, the device 104 may identify and invoke an application 112 that is capable of tracking a jogging exercise and presenting jogging-related information to the user 102. Alternatively or additionally, the application 112 may identify and notify a currently executing application 112 of a newly initiated physical activity 206. For example, the device 104 may receive from an application 112 a request to receive reports of a particular physical activity 206 (e.g., a driving application 112 may subscribe to a driving physical activity 206, and may provide a callback that the device 104 may invoke upon detecting a driving physical activity 206). The device 104 may therefore store the request, and, upon identifying the requested physical activity 206, may report the physical activity 206 to the application 112 associated with the request.

As a second variation of this third aspect, one or more applications 112 may present a flexible user interface that may adapt to the physical activity 206 of the user 102. For example, an application 112 may comprise at least two user interface modes, each associated with a different physical activity 206, and the device 104 may select the user interface mode for the user interface of the application 112 that is associated with a current physical activity 206.

Figure 7:
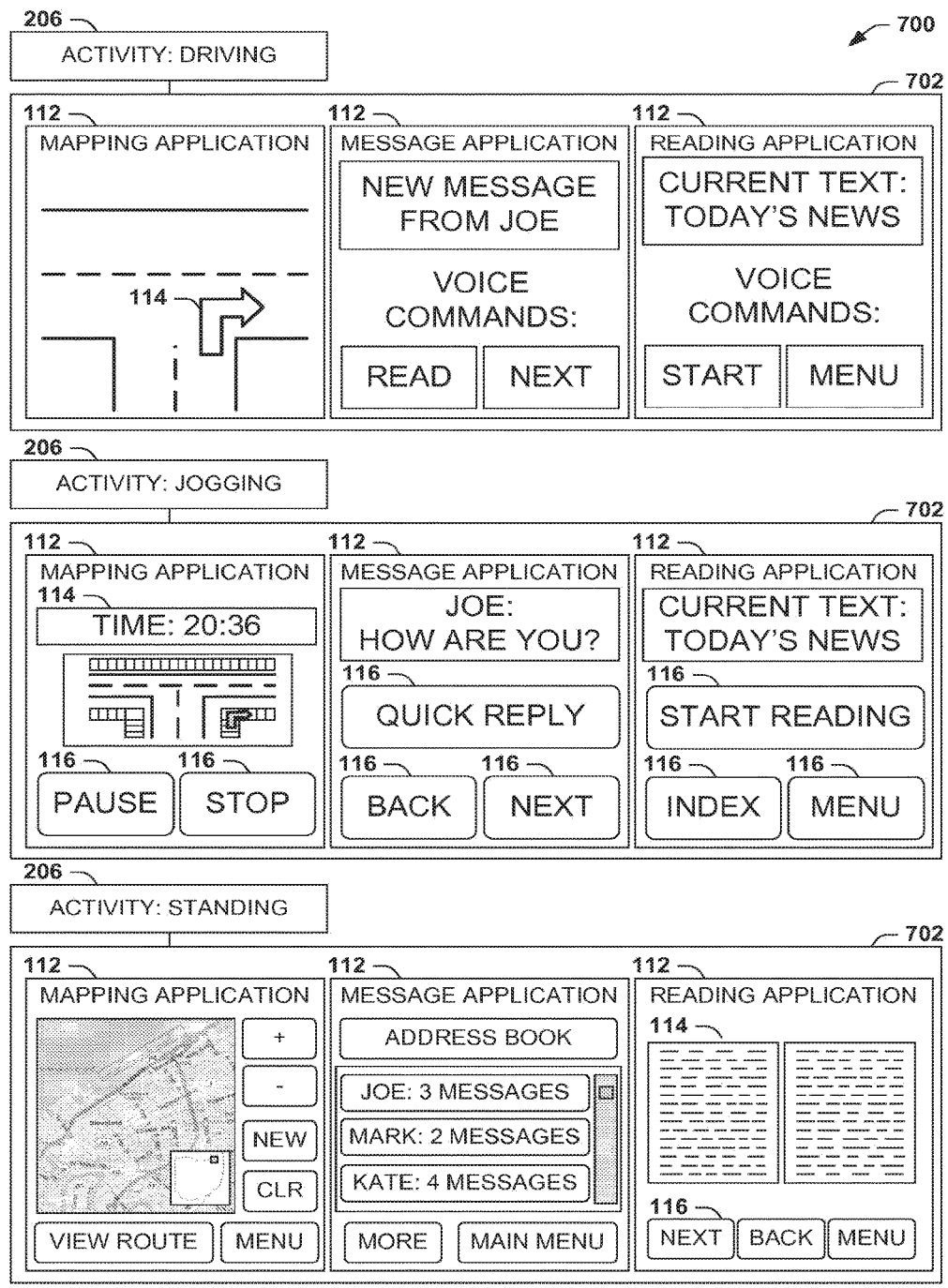
FIG. 7 is an illustration of an exemplary scenario featuring an adaptation of a set of application user interfaces in view of the physical activity of the user inferred from a set of environmental metrics.

FIG. 7 presents an illustration of an exemplary scenario 700 featuring a set of applications 112 having adjustable user interface modes 702 for respective physical activities 206. For example, when a driving physical activity 206 is detected, the applications 112 may present a user interface mode 702 comprising a constrained set of data that is highly relevant to driving, which may be presented in a large font, and may communicate with the user 102 primarily through speech-based output and speech-based user input. When a jogging physical activity 206 is selected, the applications 112 may present a second user interface mode 702, comprising information relevant to the user 102 while jogging, and large user interface controls 116 that the user 102 may select via speech-based output and touch-based user input 110 even if such user input 110 is not highly accurate. As a third example, when the device 104 detects a standing physical activity 206, the applications 112 may present a third user interface mode 702 comprising highly detailed user interface elements 114 (e.g., highly detailed maps) and plentiful user interface controls 116 that the user 102 may be able to invoke precisely while standing. In this manner, the applications 112 may utilize variable user interface modes 702 to present information relevant to the physical activity 206 of the user 102, and/or to communicate with the user 102 through input/output modalities that are suitable for the physical activity 206.

As a third variation of this third aspect, the device 104 may interact with the applications 112 and environmental sensors 106 in a manner that conserves the power of the device 104, particularly for portable devices 104 having limited power supplied by a battery or limited amount of fuel, and/or constrained computational resources. For example, the device 104 may typically keep the environmental sensors 106 powered off until receiving a request from an application 112 to identify the current physical activity 206 of the user 102. Upon receiving such a request, the device 104 may enable the at least one environmental sensor 106, detect the environmental metrics 202, and, after reporting an inferred physical activity 206 of the user 102, disable the at least one environmental sensor 106. In this manner, the device 104 may achieve the inference 204 of the physical activity 206 while also conserving power and/or computational resources. These and other techniques may be applied to utilize the physical activity 206 inferred by the device 104 in accordance with the techniques presented herein.

E. Computing Environment

Figure 8:
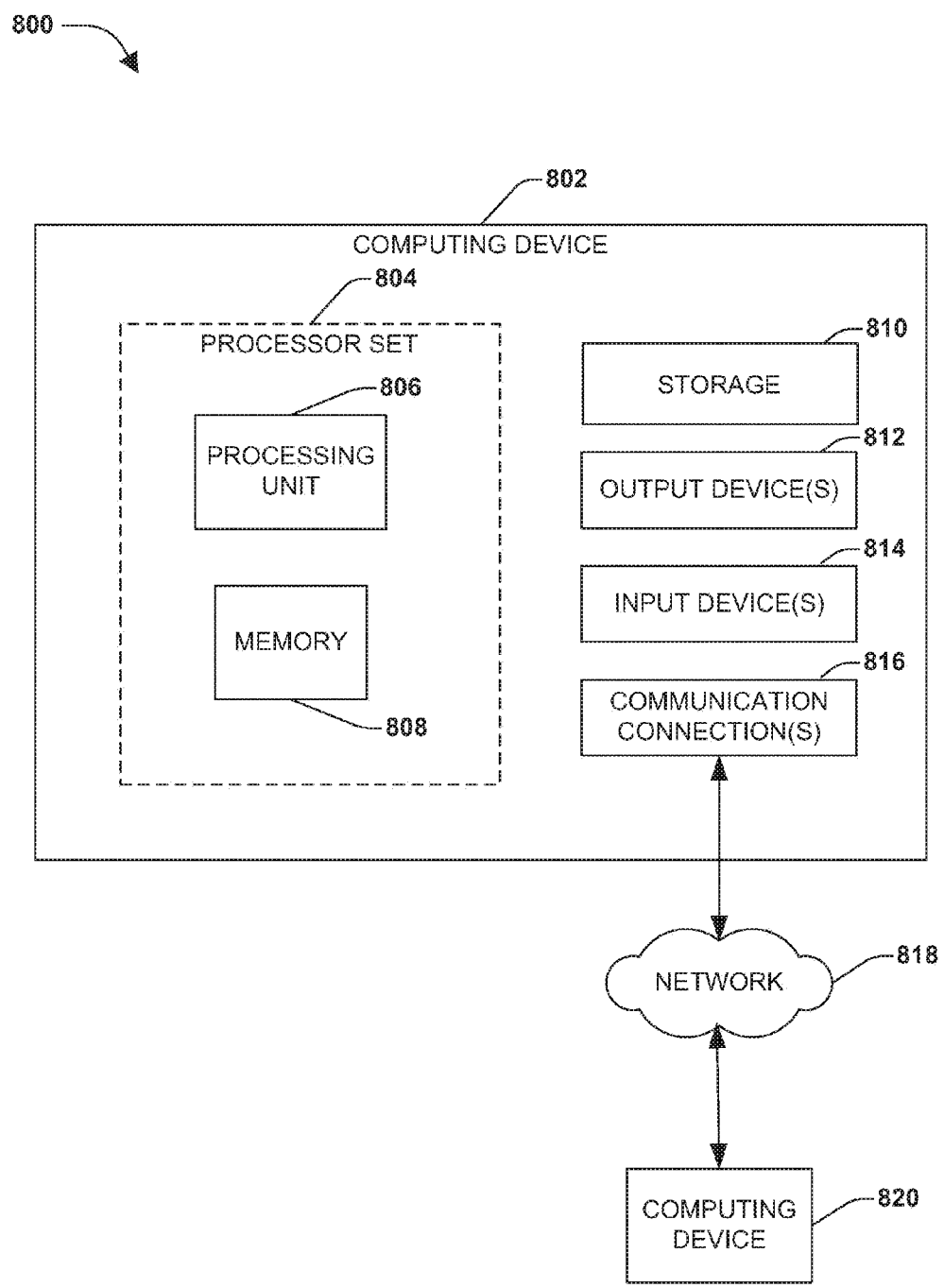
FIG. 8 illustrates an exemplary computing environment wherein one or more of the provisions set forth herein may be implemented.

FIG. 8 and the following discussion provide a brief, general description of a suitable computing environment to implement embodiments of one or more of the provisions set forth herein. The operating environment of FIG. 8 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 8 illustrates an example of a system 800 comprising a computing device 802 configured to implement one or more embodiments provided herein. In one configuration, computing device 802 includes at least one processing unit 806 and memory 808. Depending on the exact configuration and type of computing device, memory 808 may be volatile (such as RAM, for example), non-volatile (such as ROM, flash memory, etc., for example) or some combination of the two, such as the processor set 804 illustrated in FIG. 8.

In other embodiments, device 802 may include additional features and/or functionality. For example, device 802 may also include additional storage (e.g., removable and/or non-removable) including, but not limited to, magnetic storage, optical storage, and the like. Such additional storage is illustrated in FIG. 8 by storage 810. In one embodiment, computer readable instructions to implement one or more embodiments provided herein may be in storage 810. Storage 810 may also store other computer readable instructions to implement an operating system, an application program, and the like. Computer readable instructions may be loaded in memory 808 for execution by processing unit 806, for example.

The term "computer readable media" as used herein includes computer storage media. Computer storage media includes volatile and nonvolatile, removable and non-removable media implemented in any method or technology for storage of information such as computer readable instructions or other data. Memory 808 and storage 810 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 802. Any such computer storage media may be part of device 802.

Device 802 may also include communication connection(s) 816 that allows device 802 to communicate with other devices. Communication connection(s) 816 may include, but is not limited to, a modem, a Network Interface Card (NIC), an integrated network interface, a radio frequency transmitter/receiver, an infrared port, a USB connection, or other interfaces for connecting computing device 802 to other computing devices. Communication connection(s) 816 may include a wired connection or a wireless connection. Communication connection(s) 816 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 802 may include input device(s) 814 such as keyboard, mouse, pen, voice input device, touch input device, infrared cameras, video input devices, and/or any other input device. Output device(s) 812 such as one or more displays, speakers, printers, and/or any other output device may also be included in device 802. Input device(s) 814 and output device(s) 812 may be connected to device 802 via a wired connection, wireless connection, or any combination thereof. In one embodiment, an input device or an output device from another computing device may be used as input device(s) 814 or output device(s) 812 for computing device 802.

Components of computing device 802 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 802 may be interconnected by a network. For example, memory 808 may be comprised of multiple physical memory units located in different physical locations interconnected by a network.

Those skilled in the art will realize that storage devices utilized to store computer readable instructions may be distributed across a network. For example, a computing device 820 accessible via network 818 may store computer readable instructions to implement one or more embodiments provided herein. Computing device 802 may access computing device 820 and download a part or all of the computer readable instructions for execution. Alternatively, computing device 802 may download pieces of the computer readable instructions, as needed, or some instructions may be executed at computing device 802 and some at computing device 820.

F. Usage of Terms

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "exemplary" is used herein to mean serving as an example, instance, or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method for presenting a user interface for an application on an electronic device, comprising:

detecting, using a sensor associated with the electronic device, at least one metric associated with an activity performed by a user wearing the electronic device;
selecting a user interface mode based, at least in part, on the at least one metric associated with the activity;
identifying a user interface presentation that is associated with the selected user interface mode; and
presenting the user interface presentation on a display of the electronic device.

2. The method of claim 1, wherein the activity is a physical activity.

3. The method of claim 1, further comprising disabling input within the user interface presentation based, at least in part, on the activity.

4. The method of claim 1, further comprising altering an appearance of the user interface presentation based, at least in part, on the activity.

5. The method of claim 1, further comprising automatically presenting an application on the user interface, wherein the application is associated with the activity.

6. The method of claim 1, further comprising determining a confidence level that the at least one metric is associated with a particular activity.

7. The method of claim 1, further comprising associating the at least one metric with the activity based, at least in part, on received input.

8. A computing device, comprising:
at least one processor; and
a memory coupled to the at least one processor and storing instructions that, when executed by the at least one processor, perform a method, comprising:
detecting, using a sensor, at least one metric associated with a physical activity performed by an individual wearing the computing device;
determining a type of the physical activity based, at least in part, on the at least one metric;
selecting a user interface based, at least in part, on the determined type of physical activity; and
presenting the user interface on a display of the computing device.

9. The system of claim 8, further comprising instructions for determining a user interface mode based, at least in part, on the at least one metric.

10. The system of claim 8, further comprising automatically executing an application based, at least in part, on the physical activity.

11. The system of claim 8, further comprising instructions for altering an appearance of the user interface based, at least in part, on the physical activity.

12. The system of claim 8, further comprising instructions for altering input capabilities of the user interface based, at least in part, on the physical activity.

13. The system of claim 8, further comprising instructions for altering output capabilities of the user interface based, at least in part, on the physical activity.

14. The system of claim 8, further comprising instructions for determining a confidence level of the determined type of physical activity.

15. The system of claim 8, further comprising instructions for associating the at least one metric with the type of physical activity.

16. A computing device, comprising:
at least one processor; and
a memory coupled to the at least one processor and storing instructions that, when executed by the at least one processor, performs a method, comprising:

detecting, using at least one sensor, at least one metric associated with a detected activity;

selecting a user interface based, at least in part, on the at least one metric associated with the activity;

presenting the user interface on a display of the computing device; and altering input capabilities of the computing device based, at least in part, on the detected activity.

17. The system of claim 16, further comprising instructions for altering an appearance of the user interface based, at least in part, on the detected activity.

18. The system of claim 16, further comprising instructions for automatically presenting an application on the user interface, wherein the application is associated with the detected activity.

19. The system of claim 16, further comprising instructions for altering output capabilities of the computing device based, at least in part, on the detected activity.

20. The system of claim 16, wherein the detected activity is a physical activity.

* * * * *